United States Patent [19]

Mehra

[11] Patent Number: 4,941,471
[45] Date of Patent: Jul. 17, 1990

[54] RATE STABILIZATION PACEMAKER

[75] Inventor: Rahul Mehra, Stillwater, Minn.

[73] Assignee: Medtronic, Inc., Minn.

[21] Appl. No.: 241,285

[22] Filed: Sep. 7, 1988

[51] Int. Cl.⁵ .............................................. A61N 1/36
[52] U.S. Cl. ............................................... 128/419 PG
[58] Field of Search ................................. 128/419 PG

[56] References Cited

U.S. PATENT DOCUMENTS

| | | | |
|---|---|---|---|
| 3,857,399 | 12/1974 | Zacouto | 128/419 P |
| 4,163,451 | 8/1979 | Lesnick et al. | 128/419 PG |
| 4,228,803 | 10/1980 | Rickards | 128/419 PG |
| 4,388,927 | 6/1983 | Schober | 128/419 PG |
| 4,467,810 | 8/1984 | Vollmann | 128/419 PG |
| 4,485,818 | 12/1984 | Leckrone et al. | 128/419 PG |
| 4,503,857 | 3/1985 | Boute et al. | 128/419 PG |
| 4,562,841 | 1/1986 | Brockway et al. | 128/419 PG |
| 4,577,633 | 3/1986 | Berkovits et al. | 128/419 PG |
| 4,665,919 | 5/1987 | Mensink et al. | 128/419 PG |

OTHER PUBLICATIONS

Article entitled "Prevention of Ventricular Tachycardias by Automatic Rate Pacing", by F. Zacouto et al., *Rean. Art. Org.* 8, N.1, Jul. 1982, pp. 3-11.

*Primary Examiner*—Max Hindenburg
*Assistant Examiner*—Kennedy J. Schaetzle
*Attorney, Agent, or Firm*—Reed A. Duthler; Joseph F. Breimayer

[57] ABSTRACT

A cardiac pacemaker which generates stimulus pulses and senses the occurrence of natural heartbeats in a patient. The pacemaker provides for a mode of pacing rate control which tracks naturally conducted heartbeats, and responds to premature ventricular contractions. The escape interval of the pacemaker, after either a paced beat or a natural contraction, is determined by the immediately preceding escape interval, and increases with each heartbeat cycle until a predetermined lower rate is reached.

7 Claims, 4 Drawing Sheets

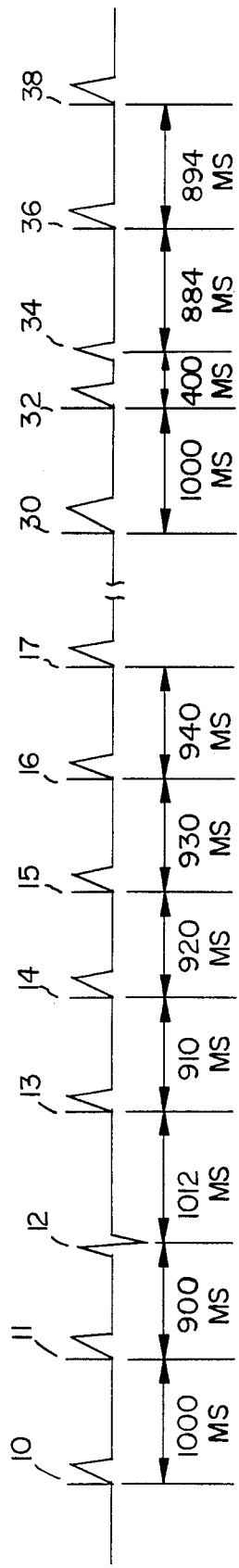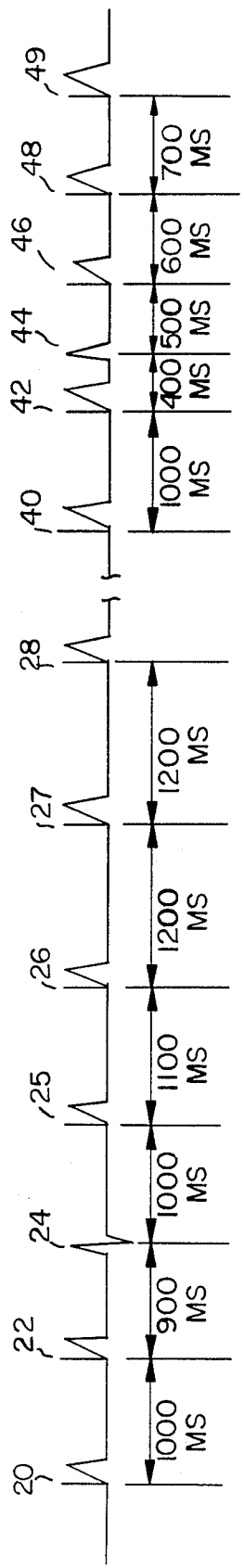

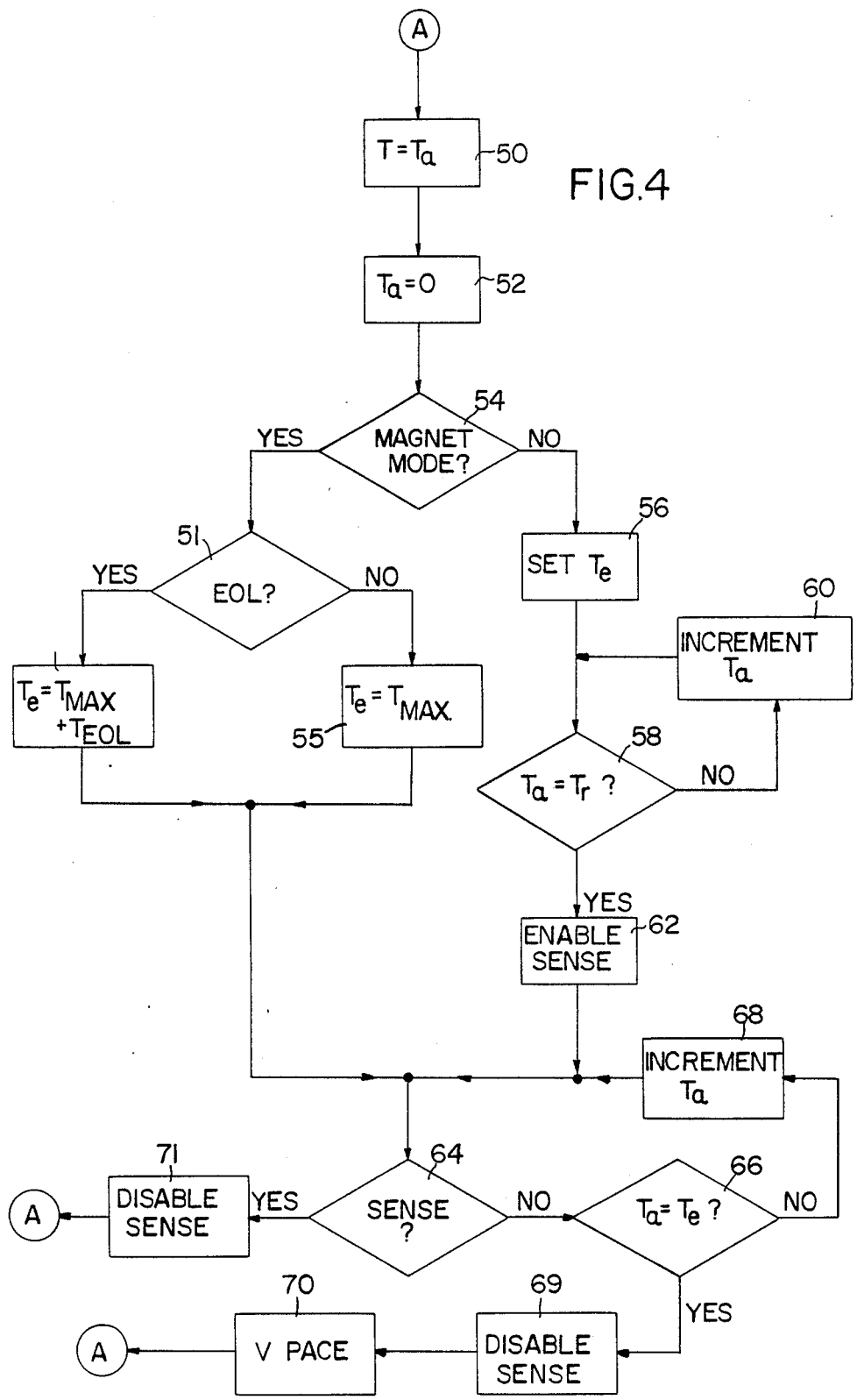

RATE STABILIZATION PACEMAKER

BACKGROUND OF THE INVENTION

This invention relates generally to cardiac stimulators and more particularly to cardiac pacemakers.

Over the years, a variety of pacing modes have been developed to respond to changes in spontaneous heart activity. One of the earliest of these is disclosed in U.S. Pat. No. 3,857,399, issued to Zacouto. Zacouto provides a system in which the underlying heart rhythm is used to control the onset of pacing, but not the pacing rate. The onset of pacing in Zacouto can occur after an interval either shorter or longer than the underlying physiologic interval.

U.S. Pat. No. 4,163,451 issued to Lesnick et al discloses a pacemaker having an overdrive pacing mode. It provides for initiation of cardiac pacing at an interval shorter than the detected cardiac interval. The stated purpose of this pacing modality is to provide a method of tachycardia treatment. Following onset of pacing, the pacing rate in Lesnick is sequentially decremented. Entry into this pacing mode at exit from its pacing mode are determined by tachycardia detection and termination criteria, so it should be expected that the overdrive pacing mode in Lesnick would be employed only occasionally.

U.S. Pat. No. 4,562,841 issued to Brockway et al discloses a dual chamber pacemaker, in which gradual increase and decrease of pacing intervals occurs in response to changes in underlying heart rate. However, adjustment of the pacing interval is primarily based on the atrial rate, rather than the ventricular. There appears to be no provision for adjusting the escape interval as a function of the measured escape interval preceding a PVC.

U.S. Pat. No. 4,503,857 issued to Boute et al discloses another cardiac pacemaker which varies its escape interval in response to the rate of underlying heart activity. This modality is referred to as "flywheel" pacing, and is intended to prevent abrupt changes in pacing rate. The system allows the pacing rate to vary with the underlying rate, but only within narrow limits. This system is designed specifically to prevent a rapid increase in pacing rate in response to a PVC or other abrupt change in heart rate.

U.S. Pat. No. 4,467,810 issued to Vollmann discloses a dual chamber pacemaker which employs a fall-back pacing mode in which ventricular pacing intervals are gradually incremented in response to a high atrial rate. The alteration of escape intervals is intended to terminate atrial tachycardias.

SUMMARY OF THE INVENTION

The present invention provides a pacemaker having a pacing mode which allows the pacemaker to follow rate changes associated with normally conducted beats and to respond quickly to the occurrence of premature ventricular contractions. Unlike overdrive pacemakers, it is not intended to detect an episode of tachycardia and terminate it. Instead, the pacemaker is intended to reduce the likelihood of the onset of an episode of tachycardia. A pacemaker according to the present invention provides an immediate change in escape interval in response to the occurrence of a PVC. The escape interval following a PVC is based on the escape interval preceding the PVC lengthened by a predetermined amount. This behavior is believed to reduce the likelihood of onset of tachycardia or fibrillation. The pacemaker displays a progressive increase in its escape interval after each heartbeat cycle, whether paced or natural, based on the length of the immediately preceding cardiac cycle. Thus, the pacemaker relatively quickly returns to its underlying pacing rate, following a PVC.

By providing a pacing interval which varies immediately in response to the length of the previous paced or sensed cardiac cycle, the pacemaker is also able to follow changes in normal heart rhythm. This can allow the heart to beat on its own a greater percentage of the time than might be possible with a similar, fixed rate demand pacemaker. Because the variation in cycle length is regular and because the variation is the same after either a heartbeat cycle ending with a paced beat or a heartbeat cycle ending with a sensed beat, proper functioning of the pacemaker is easily verified. This feature is believed to be of value, especially in circumstances in which the pacemaker's programmer is not available to receive diagnostic information which might be telemetered out of the pacemaker.

BRIEF DESCRIPTION OF THE DRAWINGS

FIG. 1 shows a simulated EKG strip illustrating the operation of the pacemaker described in the Boute et al patent cited above, in response to gradual changes in rate of normally conducted beats and in response to the occurrence of a PVC.

FIG. 2 shows a simulated EKG strip illustrating the operation of a pacemaker according to the present invention, in response to gradual changes in rate of normally conducted beats and in response to the occurrence of a PVC.

FIG. 4 is functional flow chart illustrating the basic operation of a pacemaker according to the present invention.

DETAILED DESCRIPTION OF THE DRAWINGS

Figure 3:
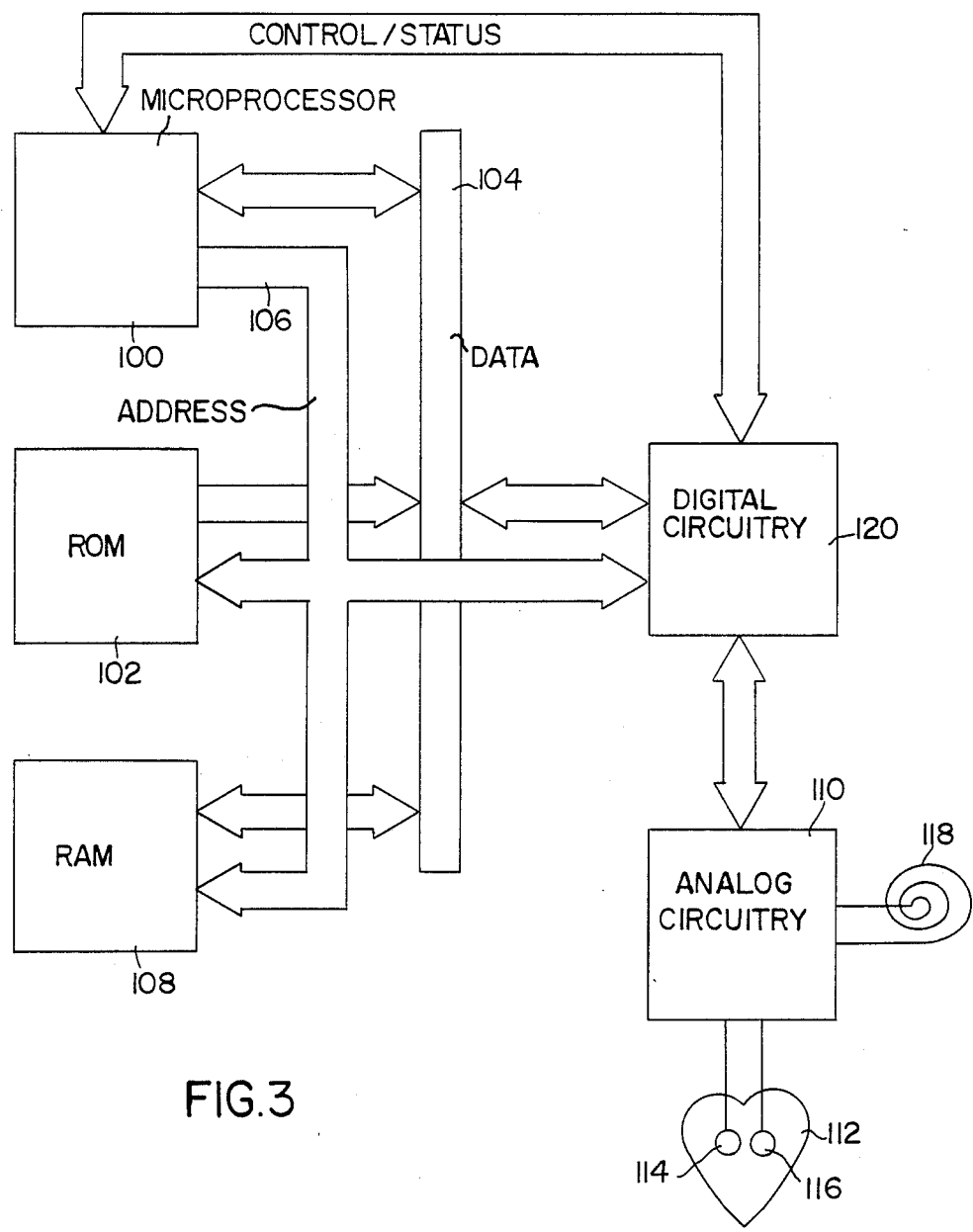
FIG. 3 is a block diagram of a pacemaker according to the present invention.

FIG. 1 illustrates the operation of the prior art "flywheel" pacing modality disclosed in U.S. Pat. No. 4,503,857 for a "PROGRAMMABLE CARDIAC PACEMAKER WITH MICROPROCESSOR CONTROL OF PACER RATE", issued Mar. 12, 1985 to Boute et al, and incorporated herein by reference in its entirety.

In the "flywheel" pacing mode, the Boute pacemaker is provided with a lower pacing rate interval ($T_{max}$), corresponding to the lowest permissible pacing rate. The pacemaker also is provided with two updatable variables which it uses in controlling the timing of pacing pulses. The first variable is $T_{ei}$, and represents the escape interval after a sensed beat. The second variable is $T_{pi}$ and represents the escape interval after a paced beat. At the end of each cardiac cycle, $T_{ei}$ and $T_{pi}$ are recalculated. After each paced beat, $T_{pi}$ is incremented by a few milliseconds, typically 0.5 ms to 10 ms, and $T_{ei}$ is set equal to $T_{pi}$. After a sensed beat, $T_{ei}$ and $T_{pi}$ are also recalculated. In response to a rapid change in cardiac cycle length, $T_{pi}$ is reduced to a predetermined fraction (0.875) of its previous value. $T_{ei}$ may be set to equal the previous value of $T_{pi}$ or the recalculated value of $T_{pi}$, depending on the method of calculation chosen. In response to a small decrease in cardiac cycle length (12.5 percent or less) or an increase in cardiac cycle length after a sensed beat, $T_{pi}$ is set equal to the length of the cycle ending in the sensed beat and $T_{ei}$ is set to be 1.125 $T_{pi}$. As such, Boute provides a pacemaker which follows an increase in heart rate, up to a maximum of 12.5 percent, and no further.

For purposes of FIG. 1, the prior art pacemaker is set at a lower rate pacing interval of 1200 ms ($T_{max}$) and employs the most aggressive rate change algorithm available. The operative pacing rate at the time the trace begins with complex 10 is 1000 ms ($T_{pi}$). After the expiration of this pacing interval ($T_{pi}$), a pacing pulse is generated at 11. The value of $T_{pi}$ is thereupon incremented by 10 ms, and a new escape interval started. At 12, a natural ventricular contraction occurs, separated by 900 ms from the previous pacing pulse at 11. At this point, the Boute pacemaker recalculates an escape interval following the sensed heartbeat 12, resulting in a new escape interval period ($T_{ei}$) of 1012 ms. The value of $T_{pi}$ is also recalculated, and is set at 900 ms.

After 1012 ms, the pacing pulse is generated at 13. At this point, $T_{pi}$ and $T_{ei}$ are both recalculated, and are set at 910 ms (previous $T_{pi}$ plus 10 ms). After this period expires, an additional paced pulse is generated at 14. The values of $T_{pi}$ and $T_{ei}$ continue to be incremented each cycle in the absence of underlying heart activity, causing paced beats at 15, 16 and 17.

In response to a normally conducted beat, an escape interval ($T_{ei}$) longer than the natural cycle length is initiated. However, when pacing begins, it will often be at a rate higher than the underlying rate, limiting the ability of the pacemaker to follow decreases in underlying heart rate.

FIG. 2 illustrates the operation of a pacemaker according to the present invention in response to changes in heart rate.

To understand the operation of a pacemaker according to the present invention, the basic timing intervals must be understood. As used herein, $T_{max}$ indicates the maximum allowable interval between a sensed beat and a paced beat or between two paced beats. $T_e$ is the escape interval that the pacemaker calculates with the beginning of each new cardiac cycle, and determines the delivery of the next pacing pulse. dT is an incremental interval used in calculation of the interval $T_e$.

For purposes of FIG. 2, the interval corresponding to the minimum pacing rate ($T_{max}$) is set at 1200 ms and the value for incrementing the pacing interval (dT) with each cycle is set at 100 ms. At the beginning of the trace at pacing pulse 20, the effective escape interval ($T_e$) is set at 1000 ms. After the expiration of this period at 22, a pacing pulse is generated and $T_e$ is incremented by 100 ms, to 1100 ms. A naturally conducted heartbeat occurs at 24, 900 ms after the paced heartbeat at 22. At this point, $T_e$ is recalculated, and set at 1000 ms (the previous natural escape interval plus 100 ms). The escape interval $T_e$ is similarly incremented by 100 ms at 25 and 26. At 26, $T_e = T_{max}$. In the absence of underlying heart activity, $T_e$ will remain at $T_{max}$, as illustrated at 27 and 28.

This illustrates the basic functioning of the pacing mode of a pacemaker according to the present invention. With the beginning of each new escape interval on the occurrence of either a paced or a sensed ventricular contraction, the subsequent pacing interval is calculated to be equal to the previous pacing interval, plus an increment dT (for example 100 ms). Incrementing continues until the escape interval $T_e$ equals the minimum pacing rate interval $T_{max}$.

FIG. 2 shows that the pacing mode of a pacemaker according to the present invention allows the pacing rate to generally track increases or decreases in the underlying heart rate. Increases in heart rate are immediately followed by a corresponding decrease in escape interval. Because the incremental value (dT) is significant, the pacemaker efficiently follows decreases in natural heart rate down to the minimum pacing rate. Moreover, the EKG strip produced by the present pacing modality is extremely easy to interpret. Every escape interval which ends with a paced beat is 100 ms longer than the previous interval until the minimum pacing rate is reached.

Returning to FIG. 1, the response of the prior art pacemaker to a PVC is illustrated. The minimum pacing rate interval $T_{max}$ is again 1200 ms. At the first paced beat 30, the current escape interval $T_{pi}$ is 1000 ms. After the expiration of this 1000 ms interval, a pacing pulse is generated at 32. $T_{pi}$ is also recalculated at this point to be 1000 ms plus 10 ms or 1010 ms. 400 ms later at 34, a PVC occurs. Because 1.125 X the cycle length preceding the PVC was less than the previous value of $T_{pi}$, the escape interval following the PVC is based on the 1010 ms escape interval ($T_{pi}$) in effect for the cycle ending in the PVC, rather than on the natural heart cycle. $T_{pi}$ is recalculated to be 0.875 times its previous value to yield a new escape interval of 884 ms. This prevents the pacemaker from rapidly responding to premature ventricular contractions. After the expiration of 884 ms at 36, the pacing interval is recalculated by adding 10 ms to $T_{pi}$, yielding a new escape interval of 894 ms, terminating at 38. This EKG strip illustrates the operation of the "flywheel", preventing rapid changes in the pacemaker's escape interval.

The pacing modality as illustrated in the second segment of FIG. 1 may also be difficult to interpret. In order to determine whether the escape interval following the PVC 34 was properly calculated, the escape interval $T_{pi}$ at 32 must be known compared with the 400 ms time interval separating beats 32 and 34 to determine which method the pacemaker would use to calculate the escape interval after PVC 34. The calculated escape interval must then be compared to the interval ending in paced beat 36.

The second portion of FIG. 2 illustrates the response of a pacemaker according to the present invention to the occurrence of a PVC. The minimum pacing rate interval $T_{max}$ is again set at 1200 ms, and the escape interval of the pacemaker $T_e$ is set at 1000 ms at initial beat 40. After the expiration of the 1000 ms escape interval at 42, the escape interval $T_e$ is recalculated to be 1100 ms. 400 ms after the paced beat at 42, a PVC occurs at 44. At this point, the escape interval Te is recalculated to be 500 ms (the actual previous escape interval plus 100 ms). Following this 500 ms escape interval, a pacing pulse is generated at 46 and the escape interval $T_e$ is recalculated to be 600 ms. 600 ms later at 48, another paced event occurs, and the escape interval $T_e$ is similarly recalculated. This trace illustrates the ability of a pacemaker according to the present invention to rapidly respond to the occurrence of a PVC. The pacemaker prevents the occurrence of an extended escape interval following a PVC, and allows the pacing rate to rapidly reapproach the minimum pacing rate.

Proper pacemaker operation following PVC 44 can be determined by simply measuring the two adjacent escape intervals and determining that the escape interval following the PVC is 100 ms longer than the one preceding the PVC. This provides a check of proper pacemaker functioning which can be performed quickly and conveniently.

FIG. 3 is a block diagram of the present invention embodied in the form of a microprocessor based pacemaker. The basic architecture set forth herein is similar to that set forth in the Boute patent, cited above. However, it is believed that one of skill in the art would be able to incorporate the present invention in microprocessor based pacemakers having differing architecture, or in pacemakers employing other analog and digital circuitry architecture. The invention is believed to reside in the method of operation, rather than in any particular physical embodiment.

The basic operation of the pacemaker is controlled by the microprocessor chip 100, under control of a stored program located in the read only memory 102. The stored program is accessed by the microprocessor via the data bus 104. Access to the read only memory 102 is controlled via the address bus 106. Programmable or alterable parameters (such as $T_{max}$) are stored in the random access memory 108. Entry of data into the random access memory 108 and read out from the random access memory 108 is controlled by microprocessor 100.

The analog circuitry 110 of the pacemaker includes an output stage which generates pacing pulses to stimulate the heart and includes a sense amplifier which detects underlying heart activity. Both the output amplifier and the sense amplifier are coupled to the heart 112 by means of electrodes 114 and 116, at least one of which is mounted to or within the heart 112. Analog circuitry 110 also includes circuitry for receiving telemetry signals from and transmitting signals to an external programmer via antenna 118. Analog circuitry 110 is under the control of digital circuitry 120. Digital circuitry 120 is controlled via control/status line 122, by microprocessor 100. Digital circuitry 120 includes one or more interval counters to facilitate timing functions and triggers the operation of the output stage in analog circuitry 110 in response to time up of the pacemaker's escape interval. Digital circuitry 120 also controls the telemetry of digital data out of the pacemaker via analog circuitry 110 and controls entry of data received by analog circuitry 110 into the microprocessor 100 and random access memory 108.

FIG. 4 illustrates a generalized flow chart of the functional operation of the pacemaker according to the present invention. Although the present invention may be configured in any of the currently available electronic technologies, including discrete components, custom logic circuitry, or microprocessor based circuitry, the preferred mode is believed to take the form of a microprocessor based pacemaker.

The pacemaker is provided with a basic, minimum pacing rate interval $T_{max}$. $T_{max}$ is preferably a programmable parameter, which defines the maximum interval which may separate a paced heartbeat from the immediately preceding sensed or paced heartbeat. In the microprocessor based embodiment illustrated in FIG. 3, an interval counter located in the digital circuitry 120 is used to determine timing intervals, much as in the above-cited Boute patent. $T_{max}$ is therefore a count which corresponds to the desired interval of time. Typically, $T_{max}$ will correspond to intervals of 600 to 1500 ms, and typically will be about 800 to 1000 ms. Similarly, $T_{min}$ is a count corresponding to the maximum allowable pacing rate (minimum pacing interval). dT is a programmable parameter corresponding to the increment of time added to each successive pacing cycle, typically 50 to 200 ms. "T" is the value of the timing interval counter stored at the point that a heartbeat cycle ends, either with a paced beat or a sensed heartbeat. "$T_a$" is the value held in the interval counter at any particular point in time. At the expiration of a heartbeat interval, this value will be reset to 0 so that counting of the next subsequent interval may begin. "$T_e$" is the variable corresponding to the pacemaker's operative escape interval. When $T_a$ equals $T_e$, a pacing pulse will be delivered. $T_{eol}$ is an interval of time, typically 100 ms or so which is added to the effective escape interval when the pacemaker detects the onset of end-of-life or battery depletion. $T_r$ is the number corresponding to the ventricular refractory period, typically 200 to 500 ms. When $T_a$ equals $T_r$, the pacemaker's sense amplifier is enabled so that it may detect the occurrence of the natural heartbeats.

The basic operation of the pacemaker is cyclic. The arbitrary starting point A is the time immediately following the delivery of a pacing pulse or the occurrence of a sensed ventricular contraction. T is set equal to $T_a$ (the actual escape interval) at 50. The interval counter is then reset at 52, with $T_a$ reset to 0. At 54, a test is done to determine whether the pacemaker is in magnet mode.

As is typical in prior art pacemakers, it is envisioned that a pacemaker according to the present invention will display end-of-life indicating behavior in response to the presence of a magnet placed over the pacemaker. Alternatively, the presence of the programming head of a cardiac pacemaker programmer over the pacemaker could be used to trigger entry into the end-of-life indicator pacing mode. The particular choice of end-of-life behavior is not critical to practicing the invention. However, in those cases in which a change in pacing rate is chosen to indicate end-of-life, it is suggested that modification of the escape interval according to the present invention should be suspended during end-of-life checking to facilitate EKG interpretation.

Assuming that a magnet or programming head is present, the pacemaker checks to determine whether battery voltage indicates that the pacer is nearing its end-of-life at 51. If battery voltage is less than a predetermined amount, the pacemaker sets the escape interval $T_e$ equal to the maximum pacing interval $T_{max}$ plus an incremental interval $T_{eol}$. If battery voltage is within normal limits, the pacemaker sets the escape interval $T_e$ equal to $T_{max}$. Because the sense amplifier is not enabled at any time when the pacemaker is magnet mode, the pacemaker will pace asynchronously with the escape interval of either $T_{max}$ or $T_{max+Teol}$, providing a convenient check to determine whether battery depletion is imminent.

Assuming that no magnet or programming head is present, the pacemaker determines the next escape interval $T_e$ at 56. The algorithm for so determining the escape interval is set forth in FIG. 5, below. After determining the escape interval $T_e$, the pacemaker checks continually to determine whether the count $T_a$ in the interval counter is equal to the refractory period count $T_r$, at 58. The interval counter continues to be incremented at 60, until $T_a$ equals $T_r$, after which time the sense amplifier 62 is enabled at 62, so that the pacemaker may sense underlying heart activity. After enabling of the sense amplifier, the pacemaker continually checks to determine whether a heartbeat has been sensed at 64 and whether the escape interval has expired at 66. Until one of these events occurs, the interval counter continues to be incremented at 68. Assuming that a ventricular contraction is sensed prior to the expiration of the escape interval $T_e$, the sense amplifier is disabled at 71, and the count $T_a$ in the interval counter is stored at 50, as discussed above. The cardiac cycle is restarted thereafter at 52, by resetting the interval counter.

If, on the other hand, the escape interval expires prior to the sensing of a ventricular contraction, the sense amplifier is disabled at 69 and a ventricular pacing pulse is generated at 70. The time at which the ventricular pacing pulse is generated is stored at 50, as discussed above, and the timing cycle is restarted at 52 by resetting the interval counter to 0.

Figure 5A:
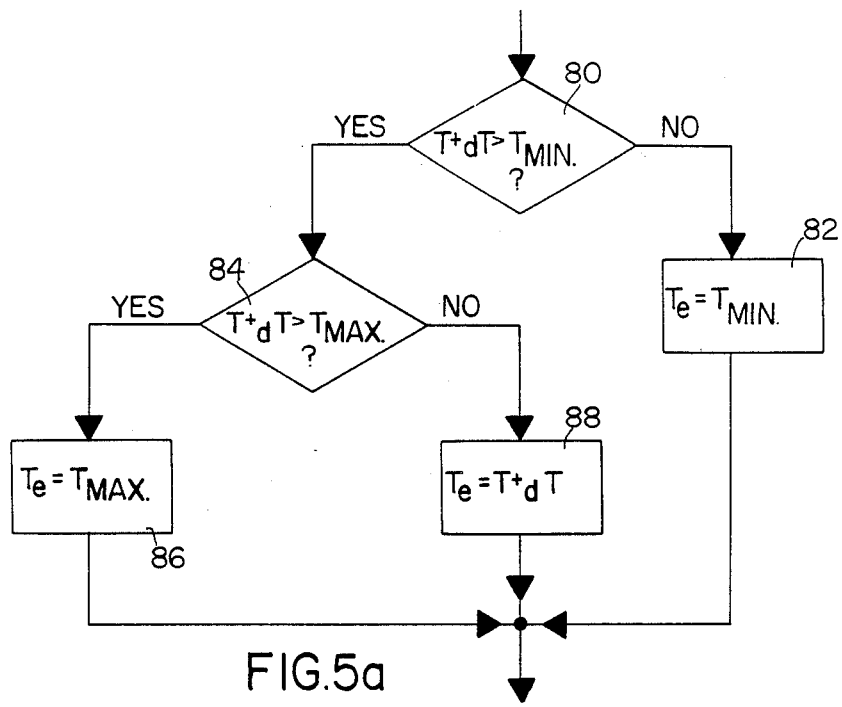
FIGS. 5a and 5b are functional flow charts illustrating two methods of controlling the pacing rate in a cardiac pacemaker according to the present invention.

FIG. 5a illustrates one method of calculating the escape interval of the pacemaker. FIG. 4a corresponds to the "SET $T_e$" step in box 56 in FIG. 3. First, the stored value T of the previous escape interval is added to the programmed increment dT at 80 to determine whether the sum of these two periods exceeds the minimum allowable escape interval $T_{min}$. If the sum of T+dT does not exceed $T_{min}$, $T_e$ is set to equal $T_{min}$ at 82. The sum of T+dT is also checked to determine whether it is greater than the maximum allowable pacing interval $T_{max}$ at 84. If the sum of T+dT exceeds the maximum pacing interval, the escape interval $T_e$ is set to equal $T_{max}$ at 86. If the sum of T+dT is between $T_{max}$ and $T_{min}$, the escape interval $T_e$ is set to equal T+dT at 88.

Figure 5B:
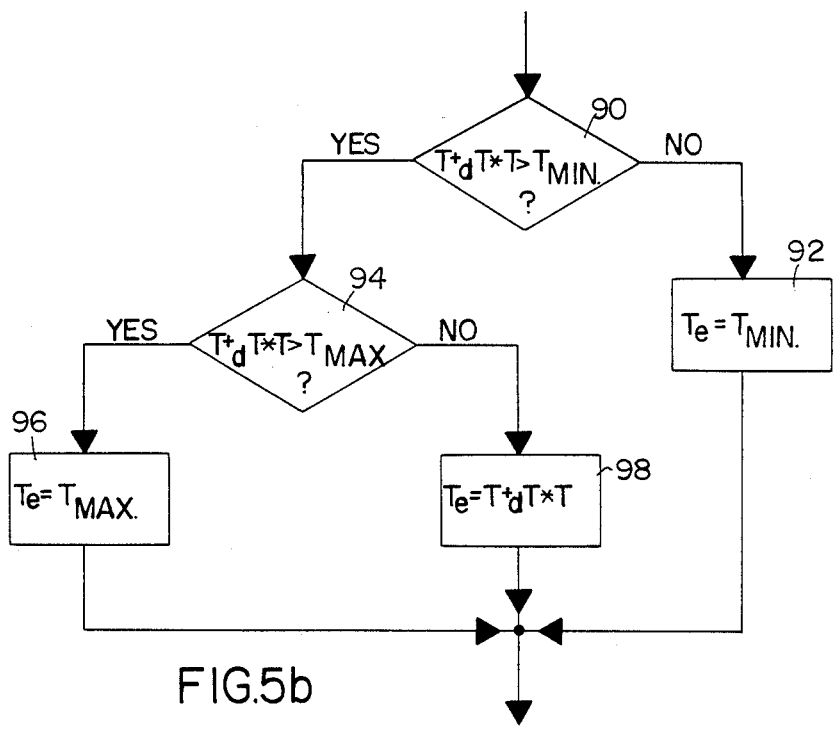

FIG. 5b illustrates an alternative method of calculating escape intervals in a pacemaker according to the present invention. In this embodiment, the incremental change from one pacing cycle to the next takes the form of a percentage change. This method of calculating escape intervals is believed to be equally therapeutic to that illustrated in FIG. 5a, but does sacrifice some of the ease of interpretation available with a fixed time increment. In this method, dT should be considered a percentage, rather than a time increment. $T+(dT \times T)$ is checked to determine that it is greater than the minimum allowable pacing interval $T_{min}$ at 90. If it is not greater than $T_{min}$, the escape interval $T_e$ is set equal to $T_{min}$ at 92. The pacemaker also checks to determine that $T+(dT \times T)$ is not greater than the maximum allowable escape interval $T_{max}$ at 94. If $T+dT \times T$ is greater than $T_{max}$, the escape interval $T_e$ is set equal to $T_{max}$ at 96. If T plus $dT \times T$ falls between $T_{min}$ and $T_{max}$, the escape interval $T_e$ is set equal to $T+(dT \times T)$ at 98.

Although the pacemaker described in the specification is a ventricular inhibited pacemaker, it is believed that the pacing modality discussed herein would also be useful and valuable in the context of a dual chamber pacemaker. For example, the present invention could be embodied in dual chamber pacemakers as disclosed in the above cited Brockway et al and Vollmann patents to allow them to respond to PVCs.

The pacemaker described in the specification employs an incremental interval dT which is the same for escape intervals $T_e$ following paced and sensed beats. It is also within the scope of the invention to use incremental intervals following paced beats which differ from incremental intervals following sensed beats. It is also within the scope of the invention to employ incremental intervals which are functions of the previous escape interval other than the simple percentage function set forth in FIG. 5b.

The present invention may also be embodied in rate responsive pacemakers of the type disclosed in U.S. Pat. No. 4,467,807 issued to Bornzin on Aug. 28, 1984, for a "Rate Adaptive Demand Pacemaker", incorporated herein by reference in its entirety. Such pacemakers vary their escape rate in response to sensing a physiologic parameter such as oxygen saturation or physical activity. In this case, it is suggested that the physiologic parameter be used to modulate $T_{max}$, with the remainder of the operation of the pacemaker as disclosed above.

In conjunction with the above specification, I claim:

1. An improved cardiac pacemaker of the type comprising:

sensing means for sensing contractions of a chamber of the heart, including premature contractions of said chamber of the heart;

pulse generating means for delivering stimulation pulses to said chamber of said heart; and timing means responsive to said sensing means and coupled to said pulse generating means, said timing means defining escape intervals following sensed contractions of said chamber, including premature contractions or following stimulation pulses applied to said chamber, and triggering said pulse generating means after the expiration of said escape intervals;

wherein the improvement comprises:

control means responsive to said pulse generating means and responsive to said sensing means for adjusting the escape interval determined by said timing means after either each sensed natural contraction of said chamber, including premature contractions or in response to the triggering of each stimulation pulse, said control means adjusting the escape interval defined by said timing means to be equal to the length of the cardiac cycle immediately preceding said sensed natural contraction or said stimulation pulse, plus a predetermined increment of time determined by said control means.

2. A pacemaker according to claim 1, wherein said predetermined increment of time determined by said control means is the same, whether said control means adjusts said escape interval in response to the triggering of a stimulation pulse or after a sensed contraction.

3. A pacemaker according to claim 1 or claim 2 wherein said predetermined increment of time determined by said control means is a fixed time interval.

4. A pacemaker according to claim 1 or claim 2 wherein said predetermined increment of time is a function of the length of the cardiac cycle immediately preceding said stimulation pulse or said sensed contraction of said chamber of said heart.

5. A pacemaker according to claim 4 wherein said predetermined increment of time is a predetermined percentage of the cardiac cycle immediately preceding said stimulation pulse or natural contraction.

6. A pacemaker according to claim 1 or claim 2 wherein said control means adjusts said escape interval within a predetermined range, such that in the event the previous cardiac cycle length plus said predetermined increment of time is less than a minimum interval, said control means adjusts said escape interval to equal said minimum interval and in the event that said previous cardiac cycle length plus said predetermined increment of time is greater than a maximum interval, said control means adjusts said escape interval to be equal to said maximum interval.

7. A pacemaker according to claim 6 wherein said pacemaker further comprises second sending means for sensing a physiologic parameter, and means for adjusting said maximum interval in response to said physiologic parameter.

* * * * *